(12) United States Patent
Ma et al.

(10) Patent No.: US 8,165,384 B1
(45) Date of Patent: Apr. 24, 2012

(54) DEFECT CLASSIFICATION

(75) Inventors: Weimin Ma, Fremont, CA (US); Carl E. Hess, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 2004 days.

(21) Appl. No.: 10/716,757

(22) Filed: Nov. 19, 2003

(51) Int. Cl.
*G06K 9/00* (2006.01)
(52) U.S. Cl. .......................................... 382/149; 382/238
(58) Field of Classification Search ................. 382/141, 382/224, 149
See application file for complete search history.

(56) References Cited

U.S. PATENT DOCUMENTS

| | | | | |
|---|---|---|---|---|
| 4,799,175 A * | 1/1989 | Sano et al. | ..................... | 382/151 |
| 5,801,965 A * | 9/1998 | Takagi et al. | ..................... | 702/35 |
| 7,079,235 B2 * | 7/2006 | Lehman | ..................... | 356/237.1 |
| 7,113,628 B1 * | 9/2006 | Obara et al. | ................... | 382/149 |
| 7,127,098 B2 * | 10/2006 | Shimoda et al. | ............... | 382/145 |

* cited by examiner

*Primary Examiner* — Hadi Akhavannik
(74) *Attorney, Agent, or Firm* — Luedeka Neely Group, P.C.

(57) ABSTRACT

A method for classifying images from a set of test images, including comparing each of the test images to reference images. Each of the test images is grouped with one of the reference images. All of the images in each group can be classified with a single classification.

23 Claims, 2 Drawing Sheets

DEFECT CLASSIFICATION

FIELD

This invention relates to the field of integrated circuit fabrication. More particularly, this invention relates to the classification of defects, such as are detected during an optical inspection of a reticle or other substrate.

BACKGROUND

The integrated circuit fabrication industry must continually produce faster and smaller devices to satisfy the expectations of the electronics industry and consumers. As the number of devices within an integrated circuit has skyrocketed, so has potential for failure of the integrated circuit increased, as a defect in any one of those millions of devices can potentially cripple the entire integrated circuit. Thus, inspections of various types, such as optical inspections, have become very important to the integrated circuit fabrication industry.

For example, integrated circuits of the type formed on monolithic semiconducting wafers, such as those formed of group IV materials such as silicon or germanium, or group III-V materials such as gallium arsenide, or combinations of such materials, are typically inspected at multiple points during the fabrication process, to ensure that material, processing, or handling problems have not created defects in the integrated circuits being formed.

However, as important as these inspections are, there are other inspections that can be even more important. For example, the patterned layers of which integrated circuits are formed are typically created with a photolithographic process, where the pattern for each layer is transferred to the wafer from a mask of some type, which is often in the form of a reticle. The reticle contains an image of the pattern that is to be transferred to the wafer. Typically, the pattern from the reticle is transferred to the wafer by optically stepping or otherwise scanning the reticle across the surface of the wafer, and exposing the pattern from the reticle onto the wafer in each of those stepped locations.

Because a single image from a reticle is used over and over again on a single wafer—perhaps hundreds or thousands of times, and is then used on many different wafers—perhaps hundreds of thousands of times, it is extremely important that the image on the reticle be as close to perfect as possible, or at the very least only have defects that are well within design parameters. Thus, the inspection of reticles is typically conducted with the very highest degree of care.

Because of the degree of care that is required, an operator is typically trained to review and classify on a one by one basis each defect that is detected by the reticle inspection system. Obviously, such a manual method of review and classification is extremely expensive and time consuming, and can easily take longer than the inspection process itself. Further, the differences in training and ability from one operator to another, and the problems associated with operator distraction or fatigue tend to introduce errors and inconsistencies into the classification process. Thus, manual classification of the defect data gathered from optical reticle inspections is somewhat unsatisfactory.

Unfortunately, automated reticle defect classification has proven to be very difficult to implement, and comes with problems of its own. For example, statistical or rule based methods of automatic defect classification can only be used in some applications, and even then these methods are generally limited by the metrics used to characterize the defect and environment and by the ability of those metrics to distinguish important differences between defects. Thus, prior art automated reticle defect classification has generally not produced adequate results, in that it tends to misclassify the defects that have been detected.

What is needed, therefore, is a system for the classification of optically detected reticle or other substrate defects that reduces or eliminates the problems described above, or other problems.

SUMMARY

The above and other needs are met by a method for classifying images from a set of test images, including comparing each of the test images to reference images. Each of the test images is grouped with one of the reference images. All of the test images in each group are classified with a single classification.

Thus, the present system reduces the workload of an inspection tool operator in the classification of defects. It does this by automatically grouping defects that are identical at a desired level of sensitivity, and allowing a single classification to result in the classification of the entire group. In this manner, the advantages of the defect classification system over manual classification is the improved speed, cost, and consistency of the classification process. The advantages of the present system over manual or rule based methods is the improved accuracy of the classification process. Thus, the methods of the invention can significantly improve the efficiency of the defect classification process and improve the cost of ownership of integrated circuit inspection tools. By reducing the number of defects that an operator needs to review in detail, there is less live review and less operator time that must be spent in the process. Further, this method enables users to operate the inspection tools at a higher sensitivity because they are less burdened by the repetitive process defects or rendering defects that might otherwise overwhelm them. Therefore, there is less fatigue induced improper classification.

In various embodiments, each of the test images is compared to absolute reference images that do not originate from the set of test images. Alternately, each of the test images is compared to floating reference images that originate from the set of test images. Preferably, a given one of each of the test images is grouped with a given one of the reference images that it most nearly matches, or placed in a new group if it does not match any of the reference images at a desired level of sensitivity. In some embodiments, all of the test images in each group are classified with a single classification that is derived from the predetermined classifications associated with the reference images by which the groups were formed. In other embodiments, one test image from each of the groups is manually inspected and classified and all of the test images for each of the groups are classified with the manually assigned classification of the one test image.

A test image is preferably combined with a reference image to produce a difference image, and if the difference image has characteristics below a desired threshold, then the test image is grouped with the reference image. Each of the test images is preferably adjusted to reduce non defect related imaging anomalies from each of the test images prior to comparing the test images to the reference images. The test images and the reference images are preferably created at a same level of resolution. Most preferably, the test images are both created and compared with the reference images at a same level of resolution. The test images are preferably images of defects on a substrate, and most preferably are images of defects on a reticle.

According to another aspect of the invention there is described a method for classifying defect images from a set of test images from a substrate, including comparing each of the test images to reference images by combining a test image with a reference image to produce a difference image. Each of the test images is grouped with the reference image that it most nearly matches as determined by the difference image, or placed in a new group if it does not match a reference image at a desired level of sensitivity. All of the test images in each group are classified with a single classification.

In various embodiments of this aspect of the invention, the test images are compared to absolute reference images that do not originate from the set of test images. Alternately, the test images are compared to floating reference images that originate from the set of test images. In some embodiments, each of the test images is adjusted to reduce non defect related imaging anomalies from each of the test images prior to comparing the test images to the reference images.

According to yet another aspect of the invention there is described a method for classifying defect images from a set of test images from a substrate, including detecting defects on the substrate using a substrate inspection tool, and creating test images of the defects on the substrate. Each of the test images is compared to reference images by combining a test image with a reference image to produce a difference image. Each of the test images is grouped with the reference image that it most nearly matches as determined by the difference image, or placed in a new group if it does not match a reference image at a desired level of sensitivity. All of the test images in each group are then classified with a single classification.

In various embodiments of this aspect of the invention, the method is performed for each of the test images in the substrate inspection tool as soon as each defect image is produced by the substrate inspection tool. Alternately, the method is performed for each of the test images in the substrate inspection tool after all of the defect images are produced by the substrate inspection tool. In some embodiments the method is performed for each of the test images on a platform that is separate from the substrate inspection tool.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
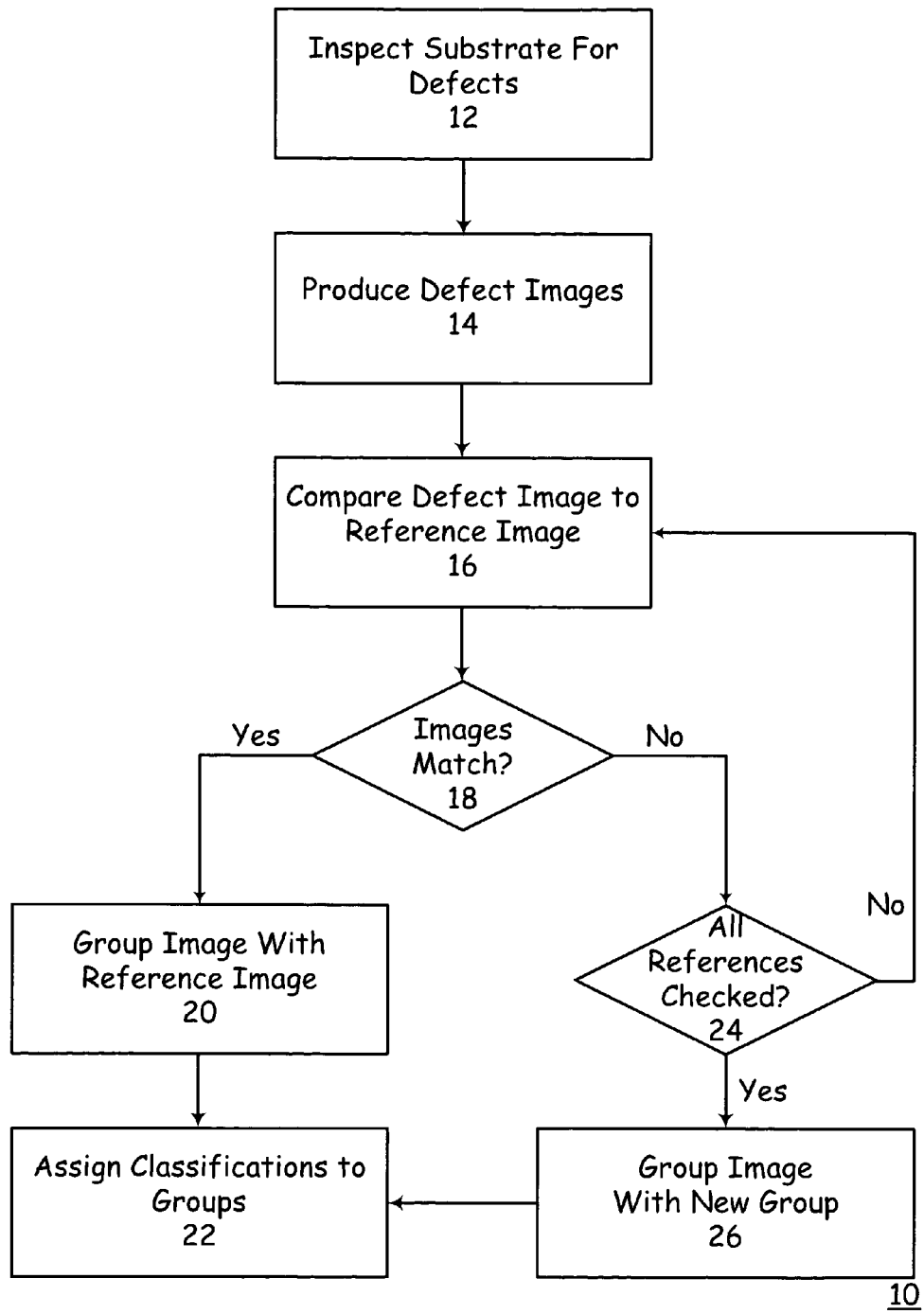
FIG. 1 is a flow chart for a method according to a preferred embodiment of the present invention.

With reference to the flow chart of the method 10 as depicted in FIG. 1, the first step of the present method is inspection of the substrate for defects, as given in block 12. It is appreciated that the term substrate is used in a generic sense in this disclosure, referring to both a wafer and a reticle. Although the most preferred application for the present invention is reticle inspection, it is appreciated that the various embodiments of the invention apply to numerous forms of inspection including wafer and other substrate inspection, and even computerized simulations of substrate inspections. For example, simulations may be used all the way from design to wafer print and compared to the desired patterns on the wafer prints. This same technique could be applied to defects found through that process.

Figure 2:
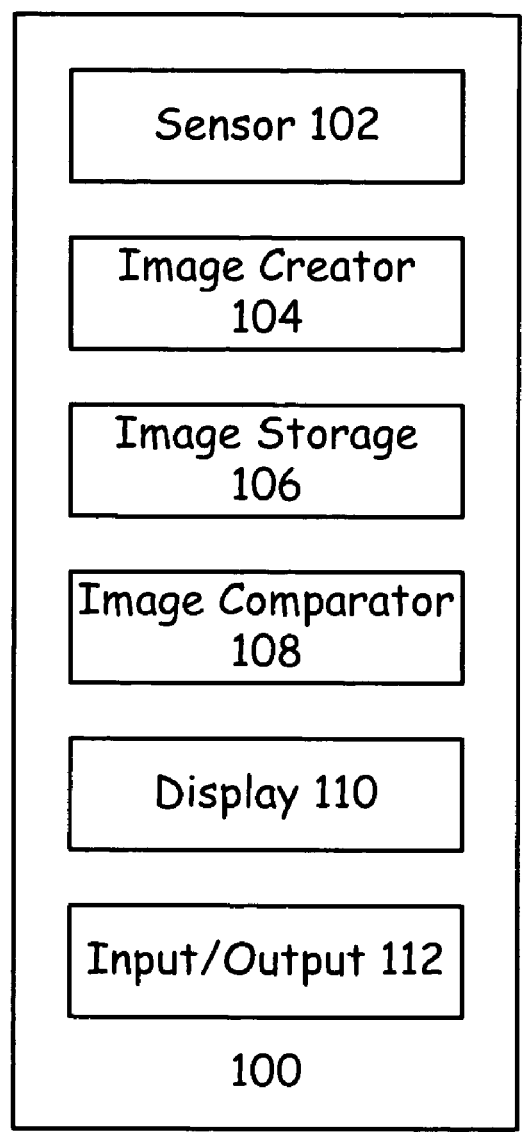
FIG. 2 is a functional block diagram of an instrument according to a preferred embodiment of the present invention.

After the inspection, images of the defects are then produced as given in block 14. The defect classification system described herein preferably uses images that include both the detected defect itself and the region on the substrate surrounding the detected defect, which images are preferably produced by an optical substrate inspection system 100 such as depicted in FIG. 2, and described in more detail below. Thus, each defect image preferably includes what is called the "reach" of the defect, which is the region of lithographic impact that the defect can influence.

Two versions of such images are preferably used in the grouping process, including a test image, which is an image that has not yet been classified, and a reference image, which is an image that contains a given type of defect, which image is used as a standard for comparison with the test image. The images of the two defects are compared, as given in block 16, to determine if the two defects and their relevant neighboring regions are equivalent within a desired threshold. If the comparison is favorable as given in block 18, then the test image is grouped with the reference image's group, as given in block 20. If the comparison is not favorable, then the test image is compared with additional reference images, as given in block 24. If the test image does not match any of the reference images at the desired threshold and sensitivity, then the test image is preferably placed into a new group as given in block 26.

The reference images can either be floating references or absolute references. By floating references it is meant that a new set of references is created with each classification process. This is accomplished by initially placing the first test image into a first group. The second test image is then compared to the first test image. If the comparison is favorable, then the second image is placed into the same group with the first image. If the comparison is not favorable, then the second image is placed into a new group. The third image is then compared to the first image, and if it does not match, then it is compared to the second image. If the third image matches either the first or second image, it is placed into the appropriate group. However, if it does not match either the first or the second image, then it is placed into a new group. This process is continued until all of the defects from the current inspection session have been grouped, at which point a classification can be assigned for each group as a whole, as given in block 22.

Alternately, an absolute method of references can be used, in which a slate of standard defect images is used for comparison to the defect images from the current inspection session. For example, the slate of standard defect images may include at least one image of each defect type that is typically encountered. Alternately, the slate of standard defect images may include at least one image of each defect type that has ever been encountered in the relevant inspection session. Further yet, the slate of standard defect images may include images of all types of defects, such as might be developed in a centralized database, such as from a single integrated circuit manufacturer, an instrument vendor, or a group of manufacturers. Preferably, each such absolute reference image represents a different defect type group.

With the absolute method of references, the first image from the current inspection session is compared with the absolute reference images, preferably one at a time, until an adequate match is determined, and the first image is then binned into that group and no further comparisons are conducted for that defect image. This process continues with the second defect image and so forth, preferably until all of the defect images from the current inspection session have been compared and grouped, at which point a classification can be assigned for each group as a whole, as given in block 22 of FIG. 1.

The comparisons for each method, being both the absolute and the floating reference methods, are preferably conducted to a selectable level. By this it is meant that the degree to which the two images must match in order for a given image to be binned with the group of the reference image is variable according to the desires of the operator, or an engineer that specifies the recipe for the comparison process. Thus, by setting the degree to be relatively lax, a so called quick and dirty grouping operation could be conducted. On the other hand, by setting the degree to be relatively stringent, a more time consuming but highly accurate and discriminating grouping operation could be conducted.

With the absolute method of references, the classification process can also be automated, as the absolute references can be previously classified. Thus, any defects which compare favorably to an absolute defect reference can be assumed, in one embodiment, to all be of the same classification as that absolute reference. The classification of the absolute reference can be determined manually, such as at a prior point in time. Thus, the classification of the test images is in this embodiment tied back to a manual classification of the reference image. However, each test image does not need to be individually and manually reviewed in order for this highly accurate manual classification to be assigned. Rather, the classifications are assigned by group.

Alternately, a manual classification could be used, such as by having an operator look at one of the images from the group, and then classifying all of the images within the group based on the classification that the operator assigns to the one, or more, inspected images. Because the operator preferably needs to inspect only one image from each group, and has a high level of confidence that each group is different, the classification process proceeds at a much faster rate than a completely manual classification process, and thus many of the problems with such a manual process are either reduced or eliminated, while the benefits of a completely manual classification process are retained.

When using the floating reference method as described above, however, the classification method is preferably not performed in an automated manner, at least not without some intervening steps. Because the defects have only been grouped according to unique groups that are present in the current inspection session, the groups do not yet have a built in or inherent classification of the defect type represented by the group, as is possible with the absolute reference image. Thus, some other method of classification is preferably employed. This method could be a manual classification, such as by having an operator look at one of the images from the group. Alternately, a representative image from each group of images could be compared one at a time to a set of absolute references, as described above, for which the classifications are known, and from which the classification for each group of the current inspection session can be assigned.

According to either the absolute or the floating reference method, defects that are deemed to be equivalent over the region of interest are preferably put into the same group. The image of a new defect is preferably compared to a single reference image from each of the existing groups until it is determined to be a member of a group, or until all groups have been compared. If the new defect does not belong to any of the existing groups, then it preferably forms a new group. If a defect is particularly large or severe, or has some other anomaly which merits independent review, then it is preferably separated and treated as a separate group for separate review.

The sensitivity at which the images are compared is preferably at least the same as the sensitivity that was used for the detection of the defects in the first place, during the inspection process, and is most preferably more sensitive. Using the same algorithms to do the comparison enables a high degree of trust in the fidelity of the comparison algorithms. In this manner, the sensitivity of the defect classification method is matched to that of the defect detection method. Preferably, the user is able to review the sensitivity used during the comparison process. For example, the maximum residual of the difference image, between the test image and the reference image, can be displayed for images within a group. Most preferably, the defects within a group are displayed in the order of reference defect image, maximum residual defect, second greatest residual defect, and so forth to the minimum residual defect. In this manner the user can check the grouping fidelity and manually ungroup defects if so desired.

One important aspect of the present method is the method by which one defect is compared with other defects, which are from either the current inspection session or from other inspection sessions. Preferably, the inspection station acquires images of the defect and the surrounding region, which images then form the basis for comparison. The images are preferably aligned to a common orientation and otherwise compensated to account for non defect related variations from one image to another. This compensation process allows the images to be compared in a manner where differences can preferably be primarily attributed to defects, and not to any of the various anomalies that may arise during the imaging process. The images are then compared one to another, and a difference image is formed. The difference image is a mathematically produced image, formed such as by logically subtracting the elements of one image from the elements in the same location in the second image. The difference image thus produced has neutral areas where the two images had identical elements disposed in identical locations, or alternately, had elements that matched within a given limit of each other, and were disposed within a given limit of location to each other.

However, elements representing the differences in the defects will preferably appear in the difference image in those locations where one of the images did not match with the other image to an acceptable degree. For example, if an optical element is present in one location of a first image, but is not present in the same or similar location of a second image, then a representation of that element will appear in the difference image, which representation tends to generally indicate the optical difference between the element that is present in the first image and not in the second image.

Preferably, various filters and thresholds are then applied to the difference image. The filters and thresholds can be selectively set to desired levels, such that differences of a relatively smaller degree can be ignored, while differences of a relatively higher degree can be retained. If the filters and thresholds remove any difference that may exist between the elements in one image and the elements in the other, then there is deemed to be no difference between the two compared defects, and they are grouped together.

As mentioned above, the method used to compare the defects is preferably at least as sensitive as the method used to detect the defects in the first place. If this is not true, then it may occur that there are defects that are indeed different, but the defect classification system is inadequately sensitive to detect the differences between them. Thus, although it is not so in every embodiment, it is preferred that the defect classification method be the same as the defect detection method, and that the classification sensitivity be at least as sensitive and most preferably more sensitive than the defect detection sensitivity.

Implementation of the defect classification system can take any one or more of a variety of different forms. For example, in one embodiment the defect classification system is online, such as within the defect inspection tool, and the comparison and grouping of defects is conducted during the inspection process as each defect is detected. Alternately, the defect classification system is implemented immediately after the end of an inspection process, but before any live review process has started, either from within the defect detection tool or from another computing platform. In yet another embodiment, the defect classification system is implemented off line after the inspection process has been completed, using images that have been stored from the inspection process, again either from within the inspection tool or from another computing platform. The choice between these approaches is a matter of system engineering tradeoffs and may be largely dependent on the computing resources available in the chosen platform.

The computational load required by the defect classification system described herein can be substantial, largely because of the number of image comparisons that may preferably take place. For example, if there are N defects that fit into M groups, then there may be as many as M*N comparisons that are made before all of defects are placed into groups. In the case where N=M, there are N(N−1)/2 comparisons. If N=2,000, then there are approximately two million comparisons. For this reason there are preferably various prescreening methods that are selectively implemented to reduce the number of full image comparisons that must be made.

For example, certain features are preferably extracted from the defect images. These features include, but are not limited to, the size, shape, and so forth of the defect image. These features are preferably used in the prescreening of the defects. Two prescreening methods are preferably used. First, if an image is so grossly defective that it is highly unlikely to be a repetitive defect, then it is placed in a group all by itself. Second, a quick, computationally inexpensive comparison of two defects is performed, such as comparing the sum of all grayscale values in image, which is used to determine whether a high fidelity comparison is necessary.

As depicted in FIG. 2, an instrument 100 according to a preferred embodiment of the present invention includes a sensor array 102, such as a camera or other sensor and associated optics for sensing images of the substrate. An image creator 104 produces an image file having information from which an optical recreation of the surface of the substrate can be generated. The instrument 100 also preferably includes an image storage 106, in which the images can be stored for at least a temporary length of time, such as while they are being formed or evaluated. An image comparator 108 compares the test images to the reference images. The test images, reference images, difference images, and other information can preferably all be selectively viewed on a display 110. An input/output 112 is preferably used to receive input for the various processing parameters and reference images, and to output test images, reference images, results, and other information.

Thus, the use of a direct grayscale comparison to classify substrate defects is a new aspect of the present invention. The use of a lithographically significant window, including the reach, over which the comparison is made, is also a new aspect of the present invention of automatic defect classification.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for classifying images from a set of test images, the method comprising the steps of:
   directly comparing each of the test images to reference images of defects,
   grouping each of the test images with one of the reference images if the test images match one of the reference images at a desired level of sensitivity, and placing the test images in a new group if the test images do not match one of the reference images at a desired level of sensitivity, and
   classifying all of the test images in each group with a single classification.

2. The method of claim 1, wherein the step of comparing each of the test images to reference images comprises comparing each of the test images to absolute reference images that do not originate from the set of test images.

3. The method of claim 1, wherein the step of comparing each of the test images to reference images comprises comparing each of the test images to floating reference images that originate from the set of test images.

4. The method of claim 1, wherein the step of grouping each of the test images with one of the reference images comprises grouping a given one of each of the test images with a given one of the reference images that it most nearly matches.

5. The method of claim 1, wherein the step of classifying all of the test images in each group with a single classification comprises classifying all of the test images in each group with a single classification that is derived from the predetermined classifications associated with the reference images by which the groups were formed.

6. The method of claim 1, wherein the step of classifying all of the test images in each group with a single classification comprises manually inspecting and classifying one test image from each of the groups and classifying all of the test images for each of the groups with the manually assigned classification of the one test image.

7. The method of claim 1, wherein the step of comparing each of the test images to reference images further comprises combining a test image with a reference image to produce a difference image, and if the difference image has characteristics below a desired threshold, then grouping the test image with the reference image.

8. The method of claim 1, wherein the step of comparing each of the test images to reference images further comprises adjusting each of the test images to reduce non defect related imaging anomalies from each of the test images prior to comparing the test images to the reference images.

9. The method of claim 1, wherein the test images and the reference images are created at a same level of resolution.

10. The method of claim 1, wherein the test images and the reference images are created at a same level of sensitivity and compared at a higher level of sensitivity.

11. The method of claim 1, wherein the test images are images of defects on a substrate.

12. The method of claim 1, wherein the test images are not images of defects on a substrate, but images of defects generated by computer simulation.

13. A method for classifying defect images from a set of test images from a substrate, the method comprising the steps of:
- comparing each of the test images to reference images of defects by combining a test image with a reference image to produce a difference image,
- grouping each of the test images with one of the reference images if the difference image is below a desired threshold, and placing each of the test images in a new group if the difference image is above the desired threshold, and
- classifying all of the test images in each group with a single classification.

14. The method of claim 13, wherein the step of comparing each of the test images to reference images comprises comparing each of the test images to absolute reference images that do not originate from the set of test images.

15. The method of claim 13, wherein the step of comparing each of the test images to reference images comprises comparing each of the test images to floating reference images that originate from the set of test images.

16. The method of claim 13, wherein the step of comparing each of the test images to reference images further comprises adjusting each of the test images to reduce non defect related imaging anomalies from each of the test images prior to comparing the test images to the reference images.

17. A method for classifying defect images from a set of test images from a substrate, the method comprising the steps of:
- detecting defects on the substrate using a substrate inspection tool,
- creating test images of the defects on the substrate,
- comparing each of the test images to reference images of defects by combining a test image with a reference image to produce a difference image,
- grouping each of the test images with one of the reference images if the difference image is below a desired threshold, and placing each of the test images in a new group if the difference image is above the desired threshold, and
- classifying all of the test images in each group with a single classification.

18. The method of claim 17, wherein the method is performed for each of the test images in the substrate inspection tool as soon as each defect image is produced by the substrate inspection tool.

19. The method of claim 17, wherein the method is performed for each of the test images in the substrate inspection tool after all of the defect images are produced by the substrate inspection tool.

20. The method of claim 17, wherein the method is performed for each of the test images on a platform that is separate from the substrate inspection tool.

21. The method of claim 1, wherein the method is performed on test images from at least one of an integrated circuit reticle, an integrated circuit substrate, and a computer simulation of a substrate.

22. The method of claim 13, wherein the substrate is one of an integrated circuit reticle, an integrated circuit substrate, and a computer simulation of a substrate.

23. The method of claim 17, wherein the substrate is one of an integrated circuit reticle, an integrated circuit substrate, and a computer simulation of a substrate.

* * * * *